United States Patent
Ollila et al.

(10) Patent No.: US 11,234,983 B2
(45) Date of Patent: Feb. 1, 2022

(54) JAK INHIBITION AS A NOVEL THERAPY FOR PREVENTING TUMORS IN PEUTZ-JEGHERS SYNDROME

(71) Applicant: Curingenetics, LLC, Ladera Ranch, CA (US)

(72) Inventors: Saara Ollila, Helsinki (FI); Tomi Mäkelä, Helsinki (FI); Eva Domenech Moreno, Helsinki (FI)

(73) Assignee: Curingenetics, LLC, Ladera Ranch, CA (US)

(*) Notice: Subject to any disclaimer, the term of this patent is extended or adjusted under 35 U.S.C. 154(b) by 0 days.

(21) Appl. No.: 16/443,386

(22) Filed: Jun. 17, 2019

(65) Prior Publication Data

US 2020/0129514 A1    Apr. 30, 2020

Related U.S. Application Data

(60) Provisional application No. 62/752,180, filed on Oct. 29, 2018.

(51) Int. Cl.
| | |
|---|---|
| *A61K 31/519* | (2006.01) |
| *A61P 35/00* | (2006.01) |
| *A61K 9/00* | (2006.01) |

(52) U.S. Cl.
CPC .......... *A61K 31/519* (2013.01); *A61K 9/0053* (2013.01); *A61P 35/00* (2018.01)

(58) Field of Classification Search
CPC .................................................. A61K 31/519
See application file for complete search history.

(56) References Cited

PUBLICATIONS

Ollila et al., Stromal Lkb1 Deficiency Leads to Gastrointestinal Tumorigenesis Involvling the IL-11-JAK/STAT3 Pathway, The Journal of Clinical Investigation, vol. 128, No. 1, pp. 402-414, Jan. 2018.*
Ruminski et al., JAK Inhibitors: New Treatments for RA and Beyond, Journal of Pharmacology and Pharmaceutical Research, vol. 2, No. 1, pp. 1-3 (Year: 2019).*
Zheng et al., Malignant Tumors Associated With Peutz-Jeghers Syndrome: Five Cases From a Single Surgical Unit, World Journal of Clinical Cases, vol. 8, No. 2, pp. 264-275 (Year: 2020).*

* cited by examiner

*Primary Examiner* — Brenda L Coleman
(74) *Attorney, Agent, or Firm* — Joseph Maenner; Maenner & Associates, LLC

(57) ABSTRACT

Treatment with the Jak1/2 inhibitor ruxolitinib results in a dramatic decrease in polyposis for organisms with Peutz-Jeghers Syndrome.

3 Claims, No Drawings

JAK INHIBITION AS A NOVEL THERAPY FOR PREVENTING TUMORS IN PEUTZ-JEGHERS SYNDROME

FIELD OF THE INVENTIONS

The inventions described below relate to the use of JAK inhibitors to treat Peutz-Jeghers Syndrome.

BACKGROUND OF THE INVENTIONS

In the United States, orphan diseases are defined as diseases that affect less than 200,000 patients. Peutz-Jeghers Syndrome (PJS) is an orphan disease.

Germline mutations in LKB1 underlie the gastrointestinal (GI) hamartomatous polyposis and increased cancer risk in Peutz-Jeghers Syndrome (PJS). PJS and other hamartomatous polyps manifest as abnormal increase in number and length of epithelial glands together with increased stroma. By contrast to two-hit tumor suppressor genes, the wild-type copy of LKB1 is typically retained in the epithelium of non-dysplastic PJS polyps and accordingly Lkb1 acts as a haploinsufficient tumor suppressor in PJS mouse models. This together with complex architecture of hamartomas has hampered studies investigating which cell type(s) initiate polyp formation. Indeed it has even been proposed that PJS polyps represent prolapses of the mucosa and not tumors at all. A role for stromal smooth muscle cells was suggested by appearance of polyps at a low frequency in mice where Lkb1 deletion was limited to smooth muscle cells. The incomplete penetrance and small polyp size however suggested that other cell types may be involved. Also Glu-Cre mediated Lkb1 deletion—aimed to target epithelial enteroendocrine L cells—was tumorigenic, but interpretation of the result was complicated by targeting also to the mesenchyme. Of note, Lkb1 loss in both epithelial and stromal cells has been shown to induce tumorigenesis in different tissue contexts, e.g. lung epithelial deletion promoting KRAS-mutant lung cancer and stromal deletion in female reproductive tract driving ovarian and endometrial tumors.

The LKB1 kinase phosphorylates and activates a number of intracellular kinases including AMPKa1-2, NUAK1-2, SIK1-3, SNRK, BRSK1-2, and MARK1-4 and thereby regulates e.g. cell metabolism and polarity in a context-dependent fashion. Despite the multitude of substrates and pathways Lkb1 has been found to regulate, it is not clear which of these are critical for suppressing gastrointestinal polyposis, although AMPK has been proposed as a likely candidate.

SUMMARY

Germline mutations in the LKB1 tumor suppressor kinase lead to gastrointestinal tumorigenesis in Peutz-Jeghers Syndrome (PJS) patients and mouse models, but the cell type(s) and signaling pathways underlying tumor formation are unknown. Recently, several reports have identified increased inflammatory signaling upon Lkb1 loss in different cell and tissue contexts, such as in skeletal muscle, macrophages, T-cells, and lung cancer, implicating Lkb1 as a suppressor of inflammatory pathways. In PJS patients and in Lkb1+/− mice, inhibition of cyclooxygenase-2 with the selective inhibitor Celecoxib demonstrated partial efficiency in reducing PJS polyposis by reducing the size but not number of tumors.

Lkb1 deletion limited to either mesenchymal progenitors (Twist2-Cre) or a subset of stromal fibroblasts (Fsp1-Cre) leads to fully penetrant polyposis. Lineage tracing and immunohistochemical analyses indicates clonal expansion of Lkb1-deficient myofibroblast-like cell foci in the tumor stroma. Loss of Lkb1 in stromal cells is associated with induction of an inflammatory program including IL-11 and activation of Jak/Stat3 pathway in tumor epithelia concomitant with proliferation. Treatment with any suitable Jak1/2 inhibitors such as ruxolitinib and itacitinib results in a dramatic decrease in polyposis.

DETAILED DESCRIPTION OF THE INVENTIONS

To investigate the role of stromal Lkb1 loss in PJS tumorigenesis two alternative strategies were used to delete Lkb1: the Twist2 (Dermo1)-Cre allele, aimed to target mesenchymal progenitor cells, and the Fibroblast-specific protein (Fsp)1-(S1004A)-Cre allele, aimed to target fibroblasts. As expected, reporter analysis in gastric mucosa, the predominant site of polyp development in PJS models, revealed that Twist2-Cre allele induced Cre expression in multiple stromal lineages including smooth muscle cells and fibroblasts. Fsp1-Cre, on the other hand, induced Cre expression in a restricted subset of gastric stromal cells. Of note, unlike the exclusively stromal activity of the Twist2-Cre knock-in allele, the recombination pattern of the transgenic Fsp1-Cre allele also revealed rare activity in epithelial stem or progenitor cells, identified by about 50 (35-65) LacZ positive gastric glands appearing across in the entire glandular stomach (representing at most 0.05% of all glands), emphasizing the importance of reporter alleles when analysing the results using transgenic Cre lines.

The Twist2-Cre and Fsp1-Cre mice were crossed with a floxed Lkb1 allele and observed both Twist2-Cre;Lkb1fl/+ (from hereon: Lkb1TwKO/+) and Fsp1-Cre;Lkb1fl/+(from hereon: Lkb1FspKO/+) mice born at expected frequency without noticeable abnormalities. To investigate the survival and possible tumor formation, the well-being of the mice over time was followed and they were euthanized when signs of discomfort were visible. All Lkb1TwKO/+mice (n=7) were euthanized latest at 16 months of age due to poor health resulting from large gastric polyps, similarly to reports from Lkb1+/− mice; mean survival being 13.3 months. In contrast, Lkb1FspKO/+mice (n=27) survived without signs of discomfort until the last point of observation at 17 months. Next, we analyzed the gastric tumor burden from Lkb1TwKO/+(n=6) and Lkb1FspKO/+mice (n=8) at 11 months of age for comparison with earlier studies. At this age, all Lkb1TwKO/+mice had developed multiple polyps (12 to 28 per mouse, average 16) demonstrating full penetrance similar to Lkb1+/− mice. Gastric polyps were also noted in Lkb1FspKO/+mice but only in 50% (4/8) of mice and with only 1.3 polyps on average per mouse indicating significantly lower tumorigenic potential, consistent with the survival analysis and low recombination frequency. As previously reported, intestinal polyps were rare in both mouse models. Remarkably, both the full penetrance and tumor burden in Lkb1TwKO/+mice were comparable to Lkb1+/− mice, demonstrating that heterozygous Lkb1 loss in stroma is sufficient for the full manifestation of PJS polyposis. Importantly, reporter analysis confirmed the exclusively stromal recombination also in the polyps of the Lkb1TwKO/+mice. The tumors in Lkb1TwKO/+mice contained limited amounts of tumor infiltrating immune cells, of which the vast majority were not recombined.

Clonally expanding of Lkb1 deficient stromal cells underlie polyp development. Next, the viability and tumorigenic potential upon homozygous loss of stromal Lkb1 expression was studied. Twist2-Cre;Lkb1fl/fl offspring were not observed, indicating embryonic lethality similarly to Lkb1 full knockout mice, whereas Fsp1-Cre;Lkb1fl/fl (Lkb1FspKO/FspKO) mice were born at expected frequencies. Remarkably, in contrast to Lkb1FspKO/+mice with low tumorigenic potential, we observed full penetrance of polyp development in the Lkb1FspKO/FspKO mice already at 4 months of age (n=19). Thus, tumorigenesis in Lkb1FspKO/FspKO mice occurs earlier than in any previously described PJS model. This result demonstrates that loss of heterozygosity (LOH) of Lkb1 increases tumorigenic potential in targeted fibroblasts, consistent with observations in smooth muscle cells. Remarkably, analysis of tumors in Lkb1FspKO/FspKO;R26R-LacZ reporter mice revealed a striking expansion of stromal Lkb1-deficient cells filling the entire polyp lamina propria, a pattern which was repeated in all studied polyps (n>20). On the other hand, the rare Cre activity in the epithelial glands driven by Fsp1-Cre allele was observed only in a subset of polyps which contained a low number of recombined glands appearing at comparable frequency as compared to the normal gastric tissue in Fsp1-Cre;R26R-LacZ reporter mice. Tumor infiltrating immune cells and smooth muscle beneath the polyps were negative for X-gal. These results strongly argue that stromal, not epithelial, loss of Lkb1 is the main driver of PJS polyps.

The rapid induction of polyposis in Lkb1FspKO/FspKO mice provided an opportunity to follow the fate of Lkb1-deficient stromal cells during tumorigenesis in Lkb1FspKO/FspKO;R26R-LacZ reporter mice. Interestingly, X-Gal staining of sections from macroscopically normal stomach of Lkb1FspKO/FspKO;R26R-LacZ mice demonstrated occasional patchy accumulation of recombined cells in lamina propria between normal-looking antral glands as well as areas with mucosal alterations containing larger number of recombined cells. In tumors, the entire stroma was filled with Lkb1-deficient cells. This observation led us to hypothesize that stroma of the polyps is composed of one or multiple clones of Lkb1-deficient stromal cells.

To test whether the increase of the Lkb1-deficient stroma resulted from clonal expansion, Lkb1FspKO/FspKO mice carrying R26R-Confetti reporter were generated. With this reporter, Cre-mediated recombination leads to expression of one of four possible fluorochromes (nuclear GFP, YFP, RFP or CFP; and areas on single color indicate clonal origin. Upon analysis of the Lkb1FspKO/FspKO;R26R-Confetti tumors, we noted large single fluorochrome expressing foci of stromal cells representing stromal clonal expansion events, indicating oligoclonal origin of the tumor stroma. By contrast, the epithelial compartment in polyps did not display clonal growth as demonstrated in polyps of Lkb1+/− mice carrying the Lgr5-EGFP-IRES-ERT2 allele with R26R-tdTomato reporter, where lineage tracing demonstrated a similar pattern in normal and tumor epithelium).

Confirming the tumors arising in Lkb1FspKO/FspKO and Lkb1TwKO/+mice as PJS polyps, histological analysis demonstrated lobular structures and branching stroma indistinguishable from Lkb1+/− and PJS polyps. The stroma of all PJS models also expressed vimentin and alpha smooth muscle actin (αSMA), indicating that the stromal cells have characteristics of activated and contractile myofibroblasts consistent with PJS polyp stroma. Notably, in all models only a subset of mesenchymal cells expressed Fsp1. The Fsp1-expressing cells were almost exclusively distinct from αSMA-expressing populations, with only 2.4% of cells expressing both markers, consistent with previous studies addressing appearance of these markers in fibroblast populations. Analysis of proliferation in polyps by Ki-67 staining indicated an expanded epithelial proliferative zone as previously noted, as well as active stromal proliferation. These results indicate that clonally expanding stromal myofibroblasts, together with reactively hyperproliferating epithelium, form polyps in PJS.

Loss of AMPK activity does not induce or augment PJS polyposis. As an initial approach to decipher molecular mechanisms underlying stromal expansion and subsequent epithelial hyperproliferation following Lkb1 loss, we investigated the possible role of AMP-activated protein kinase (AMPK). AMPK activation depends on phosphorylation by Lkb1 and AMPK has been hypothesized as a mediator of Lkb1 tumor suppressor function, mainly because of its capability to regulate mTORC1 signaling. To this end, we reasoned that if Lkb1 loss-mediated reduction of AMPK activity drove PJS polyp development, knockout mice lacking AMPK catalytic subunits AMPKα1 or AMPKα2 would develop polyps and/or augment polyposis when combined with Lkb1 heterozygosity. When analyzing the experimental cohorts, however, we noted that deletion of AMPKα1 did not result in polyp formation, nor did the Lkb1+/−; AMPKα1 double mutant show increase in tumor number or size as compared to Lkb1+/− mice. Interestingly, the tumor number in AMPKα1; Lkb1+/− mice was even lower than in Lkb1+/− mice. Deletion of AMPKα2 did not result in tumors nor modify the tumor development in Lkb1+/− mice. These results show that deletion of one the catalytic subunits of AMPK is not sufficient for polyp development, nor synergizes with Lkb1 heterozygosity to drive tumorigenesis.

Combined loss of AMPKα1 or AMPKα2 leads to embryonic lethality, prohibiting the study of full AMPK inactivity using whole-body knockout mice. Next, we took advantage of our finding that Lkb1FspKO/FspKO mice develop tumors fast with full penetrance and created AMPKa1−/−; AMPKa2FspKO/FspKO mice, displaying null AMPK activity in Fsp1-Cre expressing cells. The mice were born at expected ratios and did not display signs of declining health up to 17 months of age. Autopsy at 17 months did not reveal any tumors in contrast to Lkb1FspKO/+mice investigated at the same age. Thus, partial or complete loss of AMPK activity does not recapitulate Lkb1 loss in terms of polyposis phenotype, suggesting other pathways as critical mediators in PJS tumorigenesis.

RNA-sequencing reveals upregulation of cytokine signaling in the polyps. As a second approach to identify molecular mechanisms leading to stromal expansion and epithelial hyperproliferation, we analyzed the transcriptome from Lkb1FspKO/FspKO polyps where Lkb1 loss is biallelic and restricted to the stroma. RNA sequencing was performed from Lkb1FspKO/FspKO polyps (n=6), adjacent mucosa (n=4), and mucosa from wild-type littermates (n=5). Principal component analysis indicated marked differences between polyps and non-affected mucosa, whereas the predisposed mucosa did not separate from control. The latter results were not unexpected considering the low number of recombined cells in the predisposed gastric mucosa.

Analysis of gene expression differences in polyps compared to adjacent normal mucosa indicated 2045 significantly upregulated and 2153 significantly downregulated genes. Of these, 1104 were upregulated and 926 downregulated more than two-fold. Our results correlated well with previous microarray analyses of intestinal polyps of PJS patients and gastric polyps of Lkb1+/− mice, further validating the Lkb1FspKO/FspKO mouse as a PJS model.

Importantly, we identified substantially larger significantly altered gene sets probably due to limited patient material used previously, highlighting the usefulness of disease models where tissue specific genetic targeting may reduce the variability and help to pinpoint disease driving events from secondary changes. The RNA sequencing results and the validity of the three mouse models used in this study was further confirmed by qPCR of Wnt5a and Lrg1 (upregulated in PJS polyps), as well as Lgr5 and Grem2 (downregulated in PJS polyps) demonstrating that stromally induced polyps recapitulate the findings from PJS patients also on the molecular level.

Unbiased analysis of the deregulated gene sets indicated highest enrichment of KEGG cytokine-cytokine receptor interaction genes (upregulated) and oxidative phosphorylation genes (downregulated) in Lkb1FspKO/FspKO polyps. Similar analysis with Gene Ontology (GO) gene sets indicated highest enrichment of receptor binding genes (upregulated) and oxidoreductase activity (downregulated). In addition to increased glycolysis and reduced oxidative phosphorylation, previously reported in PJS tumors, both analyses pointed towards robust upregulation of cytokine signaling in the polyps. Importantly, combined analysis of our dataset and the previously published datasets revealed that both KEGG Cytokine-Cytokine Receptor Interaction and GO Receptor Binding sets were top hits in gene set analysis. Interestingly, Jak/Stat signaling pathway was significantly upregulated both in our RNA-seq dataset and in the PJS polyp dataset, representing the only significantly activated molecular signaling pathway identified from both signatures in this analysis. Western blotting analysis confirmed that levels of activated (phosphorylated at Y705) Stat3 were clearly elevated in polyps from both Lkb1+/− and Lkb1FspKO/FspKO mice as compared to adjacent mucosa and/or the antral mucosa from wild-type littermates. We also observed the previously noted increase in Erk1/2 phosphorylation indicating activated MAPK pathways. Interestingly, immunohistochemical analysis revealed activated Stat3 signaling not only in the Lkb1-deleted stroma, but also in the adjacent proliferative epithelium suggesting that stromal paracrine signaling leads also to epithelial Stat3 activation and proliferation in polyps.

Next, the potential paracrine factors responsible for epithelial proliferation and Stat3 activation in polyps were to be identified. A list of all genes significantly overexpressed in the RNA-seq dataset and at least one other available microarray dataset derived from PJS or Lkb1+/− mouse polyps was constructed, to enrich for core changes taking place in more than one analysis. From this list of 136 genes, the genes were selected whose products are known to be secreted, and which are expressed in the tumorigenic cell type, (myo)fibroblasts. These criteria resulted in identification of Serpine2, Il-11, Wnt5a, Cxcl14, and Ereg as top candidates. In addition, the candidate list was complimented with 11-6 and Lif, two members of IL-6 family that were upregulated in the RNA-seq analysis and are known activators of the Jak-Stat pathway. Further, Tgfb1 was included, downregulated in PJS tumors and Lkb1 deficient fibroblasts and Cxcl12 (Sdf1), described to promote tumorigenesis through secretion from cancer-associated fibroblasts (CAFs).

IL-11 as a potential activator of Jak/Stat3 signaling in polyps. We wanted to investigate which of the identified candidate genes represent primary changes caused by loss of Lkb1 in the tumorigenic cell type (fibroblasts) rather than secondary changes reflecting the complex alterations of the polyp tissue. To this end, we utilized primary mouse embryonic fibroblasts (MEFs) isolated from Lkb1fl/fl embryos and deleted Lkb1 using AdCre. qPCR analysis indicated significant upregulation of Serpine2 (1.5-fold), IL-11 (7.7-fold), Cxcl14 (7.7-fold) and IL-6 (3.8-fold) in Lkb1-deficient cells. Tgfβ1 expression was slightly but significantly downregulated, consistent with previous reports, while no significant differences were noted for Wnt5a, Ereg, Lif and Cxcl12 expression. Of genes identified to be regulated by Lkb1, IL-11 was particularly interesting as it is the critical cytokine promoting gastrointestinal tumorigenesis in several mouse models. ELISA assay confirmed that in addition to mRNA expression, also IL-11 secretion was dramatically (9-fold) increased in response to Lkb1 loss in primary MEFs. Verifying the RNAseq-results, qPCR analysis of polyps indicated a prominent upregulation of IL-11 mRNA in Lkb1+/−, Lkb1TwKO/+ and Lkb1FspKO/FspKO polyps compared to adjacent mucosa.

Despite originally identified as secreted from fibroblasts, IL-11 can also be expressed by other cell types such as immune cells. Our transcriptional profiling experiments as well as histological analysis suggested immune cell infiltration in polyps as previously described in PJS and other hamartomatous polyps. To determine whether the tumor initiating cells (fibroblasts) in the tumorigenic site (stomach) express IL-11, and whether IL-11 expression is induced by Lkb1 loss in these cells, we isolated primary gastric fibroblasts from adult (4-5 month old) Lkb1fl/fl mice and deleted Lkb1 using AdCre. Expression levels of IL-11, Cxcl14, and IL-6-genes with strongest overexpression upon Lkb1 loss in primary MEFs—were analyzed. Of these genes, IL-11 expression was significantly increased, demonstrating that Lkb1 inhibits IL-11 expression also in gastric fibroblasts. In addition, to verify that Lkb1 loss induces IL-11 expression in gastric fibroblasts also in vivo, we isolated gastric fibroblasts from two Lkb1FspKO/FspKO and one control Fsp1-Cre mice carrying the R26R-mTmG reporter where mEGFP expression indicates Cre activity and mTomato expression non-recombined cells. These cells were immortalized by continuous passaging allowing sufficient numbers for FACS sorting. The fibroblasts were sorted based on membrane fluorescent expression and measured the expression of Lkb1 and IL-11 by qPCR. It was observed that about 50% reduction of Lkb1 mRNA and 7- and 24-fold increase in IL-11 expression in mGFP population of Lkb1FspKO/FspKO but not in the control, supporting our finding that Lkb1 deficiency leads to increased levels of IL-11 in gastric fibroblasts where Lkb1 is deleted in vivo.

Next, the potential downstream pathways leading to overexpression of inflammatory cytokines upon Lkb1 deletion are investigated. Phosphorylation substrates of Lkb1 were targeted using conditional targeting (AMPKα1, AMPKα2) or small hairpin (sh)RNA approaches (Nuak1, Nuak2, Mark1, Mark2, Mark3, Mark4, Sik1, Sik2, and Sik3) and compared the transcriptional changes to Lkb1 loss induced changes in primary MEFs. Simultaneous deletion of both catalytic AMPK subunits did not result in changes in IL-11, nor of IL-6 or Cxcl14 expression consistent with our in vivo data implicating that AMPK deletion is not sufficient for polyposis. Instead, it was observed that silencing of Mark1 resulted in significant increase of IL-11 expression, and silencing of Mark4 and Sik1 led to similar trend. Cxcl14 was significantly upregulated by downregulaton of Nuak2, Mark4 and Sik1.h These results suggest that multiple downstream pathways may contribute to the increased expression of IL-11 and other pro-inflammatory factors in response to Lkb1 loss in fibroblasts, potentially including Mark1, Mark4 and Sik1-mediated effects.

IL-11 signaling is mediated via its binding to the transmembrane receptor Gp130, resulting in activation of the Jak-Stat and MAPK pathways. Of these, the induction of Jak-Stat3 activation appears most critical in GI tumorigenesis. To investigate whether IL-11 is sufficient to induce Stat3 activation in isolated wild-type epithelium, we incubated primary epithelial crypts isolated from mouse small intestine with recombinant IL-11. As expected, IL-11 resulted in activation of Stat3, comparably to IL-6. Next, we addressed whether Stat3-dependent transcriptional changes observed in polyps can be induced by IL-11 in primary epithelial organoid cultures. We focused our analysis in Reg3b, Reg3g and Lrg1 genes due to their reported expression in inflammatory epithelium in a Stat3-dependent manner and overexpression in PJS model polyps. Interestingly, IL-11 stimulation (but not IL-6) led to robust induction of Reg3b, Reg3g and Lrg1 expression, consistently with previous reports showing induction of Reg3g and Reg3b in vivo by ectopic IL-11. These results demonstrate, that IL-11 is sufficient to induce Stat3 activation and regenerative program in adjacent epithelial cells.

Pharmacological inhibition of Jak kinases reduces PJS polyp development in mice. Stat3 is phosphorylated and activated by Jak kinases which are potent drug targets for inflammatory and neoplastic diseases. The Jak1/2 inhibitor Ruxolitinib (INCB018424) has been approved for treatment of myeloproliferative diseases and is currently studied in clinical trials for treatment of several other diseases, including gastrointestinal neoplasias. To address whether the observed Stat3 activation in PJS model polyps could be targeted therapeutically by inhibiting Jak, we fed Lkb1FspKO/FspKO mice with ruxolitinib containing chow and analysed tumor burden after treatment. Intriguingly, after six weeks of treatment, 55% (6/11) of the ruxolitinib treated mice were tumor-free while all (n=11) non-treated mice developed polyps. The average tumor number was reduced to 1.27 in treated compared to 6.54 in non-treated animals. Also the average tumor area was dramatically reduced from 47.4 to 3.58 mm2 in the ruxolitinib-treated cohort. The average polyp diameter was also smaller (1.68 mm in treated vs 2.51 mm in non-treated mice), although this did not reach statistical significance (p=0.082). The drug treatment did not alter the weight of the animals, but did reduce spleen size in both Lkb1FspKO/FspKO and control mice, consistently with the efficiency of ruxolitinib in treating splenomegaly in myeloproliferative disease. These experiments uncover a central and targetable role for Jak/Stat pathway activation in PJS polyp development.

The foregoing demonstrates that loss of Lkb1 in stroma leads to clonal expansion of stromal cells and activation of an inflammatory program involving the IL-11-Jak/Stat3 pathway critical for tumorigenesis. The clonal expansion of stroma driving hyperproliferation of epithelial glands can be seen as a reversal from traditional epithelial tumors where activated but non-clonal stromal fibroblasts support the growth of clonally expanding epithelial cells, and is interesting in light of previous suggestions of genetic co-evolution and even initiating roles proposed for stroma. Our findings are supported by the lack of clonal growth of polyp epithelium addressed in this study, and in PJS polyps previously analyzed with HUMARA assay. Also the observation that deletion of Lkb1 in gastrointestinal epithelial cells does not result in a significant decrease in mouse lifespan and that Lkb1 loss from smooth muscle cells using Tag1n-CreERT2 led to development of PJS type polyps, strongly support our view that stroma is the critical site of tumor suppression by Lkb1. This along with Fsp1-Cre and earlier with Tag1n-CreERT2 suggest that homozygous deletion of Lkb1 in stroma enhances tumorigenicity while heterozygous deletion is sufficient for polyposis.

The foregoing observations expand the findings deciphering the complex interplay of epithelium and stroma in hamartomatous tumors. In juvenile polyposis syndrome caused by mutations of SMAD4 second hits are not required for polyposis or progression and either the epithelial component alone or together with the mesenchyme drives tumorigenesis based on clonality analysis. In PTEN hamartoma tumor syndrome (PHTS/Cowden Syndrome) polyposis is initiated by PTEN-deficient epithelial stem cells, and epithelial loss of PTEN is sufficient for polyposis and to recapitulate PHTS features suggesting a secondary role for the stroma. By contrast, in tuberous sclerosis hamartomas, biallelic stromal deletion of TSC1 or TSC2 drives hamartoma formation through induction of paracrine factors activating the adjacent epidermis. Together these results indicate gene- and context-specific etiologies for hamartomas and suggest that studies on hamartomas will provide insights into tissue morphogenesis, regeneration and mesenchymal-epithelial interactions.

Regarding the stromal deletion approaches resulting in PJS polyps, Twist2-Cre is widely expressed in mesenchymal lineages, while Fsp1-Cre and Tag1n-CreERT2 mainly target different cell types (fibroblasts vs mature smooth muscle, respectively), raising a question about the stromal cell type(s) able to initiate PJS polyposis. On one hand, differentiation program towards the tumorigenic myofibroblast could be initiated in different contexts following Lkb1 deletion; alternatively, the deletors may overlap in expression. Consistent with the latter model, Tag1n can be expressed in a gastric myofibroblasts and thus, it is possible that myofibroblasts represent the tumorigenic cells in all PJS models.

The induction of an inflammatory program and Jak/Stat signaling was a major alteration in PJS and mouse model polyps noted in unbiased analyses in this study. This finding was interesting considering that secretion of inflammatory cytokines, many with capacity to trigger Jak/Stat pathway activation, represents an important tumor-promoting mechanism of activated fibroblasts, suggesting that similar activities may be important in the fibroblast-epithelium interplay in PJS polyps. Intrestingly, a recent study distinguished two populations of cancer-associated fibroblasts (CAFs) in pancreatic cancer: CAFs with high expression of αSMA (termed myCAFs) and CAFs with lower levels of αSMA (termed iCAFs). The iCAF cells expressed high levels of inflammatory cytokines and induced Jak/Stat signaling in pancreatic epithelial cells. Considering that loss of Lkb1 in mesenchymal cells leads both to a reduced expression of αSMA and induces an inflammatory signature (this study), it would be interesting to study whether the iCAF population in PC shares other similarities with Lkb1-deficient fibroblasts in PJS polyps.

Emphasizing the importance of activated Stat3 signaling in gastrointestinal tumorigenesis, mice carrying a Stat3 activating mutation in the Gp130 gene develop tumors in the gastric antrum, representing also the most frequent site of PJS type polyp development. Gp130 is the receptor for IL6-family cytokines, including IL-11. Regarding the mechanisms of Stat3 activation in PJS models, we showed here that Lkb1-deficient fibroblasts express and secrete increased amounts of IL-11, which was also strongly upregulated in polyps and sufficient to induce epithelial Stat3 activation. Further, recombinant IL-11 but not IL-6 induced a set of Stat3-dependent epithelial genes in cultured epithelial organoids; this set was also upregulated in polyps. Notably, previous studies have demonstrated the importance of IL-11 in gastrointestinal tumorigenesis: the antral tumorigenesis in the gp130 mutant mice can be blocked by deletion of the gp130 co-receptor IL11Ra critical for IL-11 signaling, but not by deleting IL-6. IL-11 signaling appears to play an important role also in colitis-associated colon cancer as well as in intestinal tumorigenesis in Apc-min mice. In the future, it would be interesting to address the requirement of IL-11 to PJS tumorigenesis by deleting Lkb1 together with Il11 from stromal fibroblasts.

The finding that Jak inhibition using s dramatically reduced polyp development in Lkb1FspKO/FspKO mice confirmed that activated Jak/Stat signaling is a central pathway driving polyposis. Previous preclinical studies using COX-2 inhibitor celecoxib and mTOR inhibitor rapamycin have not resulted in a comparable reduction, and could partly represent unspecific inhibition of growth. The mechanistic studies indicating that the AMPK-mTOR axis is not sufficient for polyposis and rather implicating cooperation of other Lkb1 substrate kinases may partly explain these results. The identification of a clinically approved Jak inhibitors such as ruxolitinib that efficiently inhibits tumorigenesis in PJS models suggests therapeutic opportunities also for PJS patients.

In summary, the foregoing demonstrates, that PJS polyposis is a stromal disease mediated by abnormal stroma-epithelium crosstalk including activated IL-11-Jak/Stat3 axis. These findings significantly advance our knowledge on PJS, provide therapeutic opportunities, and may have broader implications on other tumors. These results indicate clonal expansion of stromal cells and activation of Jak/Stat3 signaling in polyps, and indicate therapeutic efficacy with suitable Jak inhibitors to treat the symptoms of Peutz-Jeghers Syndrome.

The ruxolitinib (INCB18424, Incyte) treatment was done in littermate male and female Lkb1FspKO/FspKO mice.t The drug was given orally as a chow mixed in the LabDiet #5002 Rodent Chow in the ratio of 2 g of ruxolitinib to 1 kg of chow as previously described except that the treatment period was 6 weeks (n=11, 6 females and 5 males). The control group (n=11, 5 females and 6 males) received LabDiet #5002 Rodent Chow without ruxolitibib for 6 weeks. Both groups were fed ad libitum. Wild-type (Lkb1fl/fl without Cre allele) littermate mice were also treated with ruxolitinib and control diet (n=5 each, 3 females and 2 males) for 6 weeks to control for adverse effects. At the endpoint, body weight and spleen weight were recorded and tumor number and size counted.

Any suitable Jak inhibitor such as Itacitinib (IBI-377; INCB-039110; INCB-039110-adipate; INCB-39110; Itacitinib-adipate), Ruxolitinib (trade names Jakafi/Jakavi), Tofacitinib (trade names Xeljanz/Jakvinus, formerly known as tasocitinib and CP-690550), Oclacitinib (trade name Apoquel) and Baricitinib (trade name Olumiant) may be used. Other suitable Jak inhibitors that may be used are currently undergoing clinical trials and/or experimentation or have shown some efficacy such as Filgotinib (G-146034, GLPG-0634), Cerdulatinib (PRT062070), Gandotinib (LY-2784544), Lestaurtinib (CEP-701), Momelotinib (GS-0387, CYT-387), Pacritinib (SB1518), Upadacitinib (ABT-494), Peficitinib (ASP015K, JNJ-54781532), Fedratinib (SAR302503), Cucurbitacin I (JSI-124), Tofacitinib, topical tofacitinib and ruxolitinib for alopecia, Topical ruxolitinib for Vitiligo, Decernotinib (Previously known as VX-509), GLPG0634, CEP-3377929,30, R348, Fibotinib (GLPG0634), Decernotinib (VX-509), ABT-494, AG-490, MS-1020, TG101348, STA-21, Stattic and WP1066.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method of treating a patient with Peutz-Jeghers Syndrome comprising the step: administering a therapeutic dose of ruxolitinib to the patient.

2. The method of claim 1 wherein the step of providing a therapeutic dose is accomplished via an oral dosage.

3. The method of claim 1 wherein the administering step further comprises cyclically administering a therapeutic dose of ruxolitinib to the patient.

\* \* \* \* \*